(12) United States Patent
Nagano et al.

(10) Patent No.: US 7,939,330 B2
(45) Date of Patent: May 10, 2011

(54) FLUORESCENT PROBE

(75) Inventors: Tetsuo Nagano, Tokyo (JP); Eita Sasaki, Tokyo (JP); Hirotatsu Kojima, Tokyo (JP); Tomoya Hirano, Tokyo (JP); Kazuya Kikuchi, Kanagawa (JP)

(73) Assignee: Tetsuo Nagano, Tokyo (JP)

( * ) Notice: Subject to any disclaimer, the term of this patent is extended or adjusted under 35 U.S.C. 154(b) by 0 days.

(21) Appl. No.: 12/911,348

(22) Filed: Oct. 25, 2010

(65) Prior Publication Data

US 2011/0038803 A1 Feb. 17, 2011

Related U.S. Application Data

(63) Continuation of application No. 10/598,250, filed as application No. PCT/JP2005/002753 on Feb. 22, 2005, now abandoned.

(30) Foreign Application Priority Data

Feb. 23, 2004 (JP) ................................. 2004-045643

(51) Int. Cl.
*G01N 21/78* (2006.01)
*G01N 31/00* (2006.01)
*G01N 31/22* (2006.01)
*C07D 209/08* (2006.01)
*C07D 249/18* (2006.01)

(52) U.S. Cl. ............ 436/81; 436/92; 436/546; 436/800; 548/455; 548/259

(58) Field of Classification Search .................... 436/81, 436/92, 546, 800; 548/455, 259
See application file for complete search history.

(56) References Cited

U.S. PATENT DOCUMENTS

| | | | |
|---|---|---|---|
| 5,440,042 A | 8/1995 | Fabricius et al. | |
| 5,445,672 A | 8/1995 | Closs et al. | |
| 5,571,388 A * | 11/1996 | Patonay et al. | 204/461 |
| 5,874,590 A | 2/1999 | Nagano et al. | |
| 6,201,134 B1 | 3/2001 | Nagano et al. | |
| 6,593,148 B1 * | 7/2003 | Narayanan | 436/546 |
| 6,995,274 B2 * | 2/2006 | Lugade et al. | 548/427 |
| 7,504,089 B2 * | 3/2009 | Lugade et al. | 424/9.6 |
| 7,597,878 B2 * | 10/2009 | Kovar et al. | 424/9.6 |
| 2003/0162298 A1 | 8/2003 | Nagano et al. | |
| 2004/0235902 A1 | 11/2004 | Nagano et al. | |
| 2006/0030054 A1 | 2/2006 | Nagano et al. | |
| 2006/0128961 A1 | 6/2006 | Timpe et al. | |
| 2006/0275912 A1 | 12/2006 | Nagano et al. | |
| 2007/0298507 A1 | 12/2007 | Nagano et al. | |
| 2008/0014602 A1 | 1/2008 | Nagano et al. | |

FOREIGN PATENT DOCUMENTS

| | | |
|---|---|---|
| CA | 2128815 | 5/1996 |
| EP | 1221465 | 7/2002 |
| JP | 3-200024 | 9/1991 |
| JP | 7-3177 | 1/1995 |
| JP | 7-150056 | 6/1995 |
| JP | 10-226688 | 8/1998 |
| JP | 11-505533 | 5/1999 |
| JP | 2000-239272 | 9/2000 |
| JP | 2000-321262 | 11/2000 |
| JP | 2003-277385 | 10/2003 |
| JP | 2004-190000 | 7/2004 |
| WO | 99/01447 | 1/1999 |
| WO | 01/62755 | 8/2001 |

OTHER PUBLICATIONS

D. Gallaher et al., "Development of Near-Infrared Fluorophoric Labels for the Determination of Fatty Acids Separated by Capillary Electrophoresis with Diode Laser Induced Fluorescence Detection", Analyst, vol. 124, No. 11, pp. 1541-1546 (1999).

M. Lipowska et al., "New Near-Infrared Cyanine Dyes for Labeling of Proteins", Synthetic Communications, vol. 23, No. 21, pp. 3087-3094 (1993).

J. Flanagan Jr. et al., "Functionalized Tricarbocyanine Dyes as Near-Infrared Fluorescent Probes for Biomolecules", Bioconjugate Chemistry, vol. 8, No. 5, pp. 751-756 (1997).

S. Miltsov et al., "Boron Trifluoride-Methanol Complex-Mild and Powerful Reagent for Deprotection of Labile Acetylated Amines", Tetrahedron Letters, vol. 44, No. 11, pp. 2301-2303 (2003).

English Language abstract of JP 2003-277385.

English Language abstract of JP 2000-321262.
English Language abstract of JP 2000-239272.
English Language abstract of JP 3-200024.
U.S. Appl. No. 10/570,355 (Nagano et al.), filed Mar. 3, 2006 and entitled, "Fluorescent Probe".
Gallaher, Jr. Anal. Chem. 2000, 72(9) pp. 2080-2086.
Narayanan et al., J. Org. Chem., (1995), 60(8) pp. 2391-2395.
Strekowski et al., J. Org. Chem., (1992), 57(17) pp. 4578-4580.
Japanese Office Action mailed Nov. 24, 2010, and partial English Translation.

\* cited by examiner

*Primary Examiner* — Robert J Hill, Jr.
*Assistant Examiner* — Dwan A Gerido
(74) *Attorney, Agent, or Firm* — Greenblum & Bernstein, P.L.C.

(57) ABSTRACT

A fluorescent probe which specifically and efficiently traps nitrogen monoxide, zinc ion etc. to emit fluorescence is provided.
A compound represented by the following general formula (I):

[Formula 1]

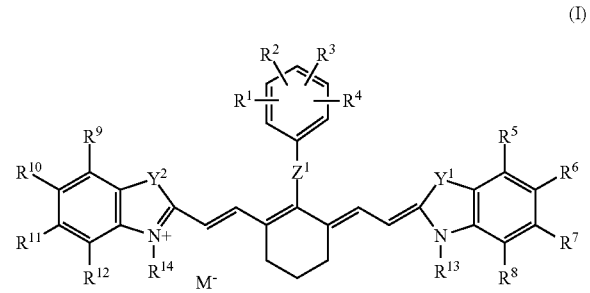

[wherein $R^1$ and $R^2$ represent hydrogen atom, or a group represented by the following formula (A):

[Formula 2]

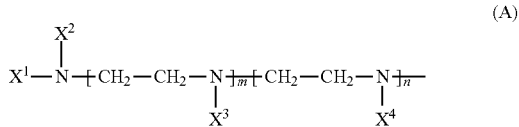

(wherein $X^1$ to $X^4$ represent hydrogen atom, an alkyl group, or a protective group for amino group, and m and n represent 0 or 1); $R^3$ and $R^4$ represent hydrogen atom, a $C_{1-6}$ alkyl group, or a $C_{1-6}$ alkoxy group; $R^5$ to $R^{12}$ represent hydrogen atom, sulfo group, phospho group, a halogen atom, or a $C_{1-6}$ alkyl group; $R^{13}$ and $R^{14}$ represent a $C_{1-18}$ alkyl group; $Z^1$ represents oxygen atom, sulfur atom, or —N($R^{15}$)— (wherein $R^{15}$ represents hydrogen atom, or a $C_{1-6}$ alkyl group); $Y^1$ and $Y^2$ represent —C(=O)—, —C(=S)—, or —C($R^{16}$)($R^{17}$) (wherein $R^{16}$ and $R^{17}$ represent a $C_{1-6}$ alkyl group); and $M^-$ represents a counter ion in a number required for neutralizing the charge].

4 Claims, 3 Drawing Sheets

FLUORESCENT PROBE

CROSS-REFERENCE TO RELATED APPLICATIONS

This application is a continuation of application Ser. No. 10/598,250 filed May 29, 2007, now abandoned which is a national stage of PCT/JP2005/002753, filed Feb. 22, 2005, which claims priority to Japanese Application No. 2004-045643, filed Feb. 23, 2004. The disclosures of application Ser. Nos. 10/598,250 and PCT/JP2005/002753 are incorporated by reference herein in their entireties.

TECHNICAL FIELD

The present invention relates to a fluorescent probe. More specifically, the present invention relates to a fluorescent probe which traps nitrogen monoxide, zinc ion, and the like to emit fluorescence.

BACKGROUND ART

Recently, it has been reported that particular fluorescein derivatives, that per se have almost no fluorescent property, readily react with nitrogen monoxide under a neutral pH condition to provide a triazole compound having a strong fluorescence intensity, and the triazole derivative can emit intense fluorescence at a wavelength of around 515 nm under excitation light at a long wavelength of around 495 nm (Kojima et al., the 16th Medicinal Chemistry Symposium, the 5th Annual Meeting of the Pharmaceutical Chemistry Section, the Lecture Abstracts, pp. 166-167, Subject No. 2-P-26, published by the Pharmaceutical Society of Japan, Oct. 23, 1996). When these fluorescein derivatives are used as an agent for nitrogen monoxide measurement, the excitation light can be easily cut off with a fluorescence filter provided on an ordinary fluorescence microscope, and intracellular nitrogen monoxide concentration can be conveniently measured by measuring fluorescence in individual cells. However, lights in the visible region having a wavelength of around 500 nm are significantly absorbed by living tissues, and therefore, they are disadvantageous for in vivo imaging of nitrogen monoxide, and they also have a problem that regions for which imaging can be performed are limited to those around the epidermis. For this reason, it is desired to develop a probe which exhibits high transmission for living tissues and can be excited with a near-infrared light of a wavelength around 650 to 950 nm.

Zinc is an essential metallic element that is present in the human body in the largest amount next to iron, and most zinc ions in cells strongly couple to proteins and are involved in the maintenance of structures of proteins or in the expression of functions of the proteins. Various reports have also been made on the physiological role of free zinc ions, which are present in cells in a very small quantity (generally at a level of μM or lower). In particular, zinc ions are considered to be deeply involved in apoptosis, which is one of cell death processes, and it has also been reported that zinc ions accelerate senile plaque formation in Alzheimer's disease, for example. As for zinc ions, fluorescent zinc probes described in International Patent Publication WO01/62755 have been proposed as fluorescent probes for zinc which can measure zinc ions with high sensitivity and cause no cell injury
[Patent document 1] Japanese Patent No. 3200024
[Patent document 2] International Patent Publication WO01/62755

DISCLOSURE OF THE INVENTION

Object to be Achieved by the Invention

An object of the present invention is to provide a fluorescent probe which specifically and efficiently traps nitrogen monoxide, zinc ion and the like to emit fluorescence, and thus provide a fluorescent probe which enables imaging of a deep portion of a living body. More specifically, the object of the present invention is to provide a fluorescent probe which can be excited with near-infrared lights having a wavelength of around 650 to 950 nm, which are highly permeable in living tissues.

The inventor of the present invention energetically tried to achieve the aforementioned object, and as a result, found that the non-fluorescent compounds represented by the following general formula (I) very efficiently trapped nitrogen monoxide or zinc ion to change into fluorescent substances, and when the fluorescent substances were excited with near-infrared lights of around 650 to 950 nm, highly intense fluorescence was obtainable. The inventor also found that nitrogen monoxide or zinc ion in deep tissues of living body was measurable with extremely high sensitivity by using these compounds. The present invention was accomplished on the basis of these findings.

The present invention thus provides a compound represented by the following general formula (I):

[Formula 1]

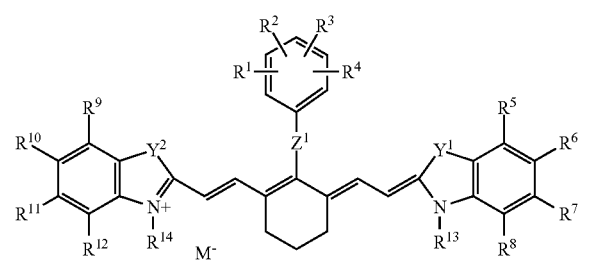

[wherein $R^1$ and $R^2$ independently represent hydrogen atom, or a group represented by the following formula (A):

[Formula 2]

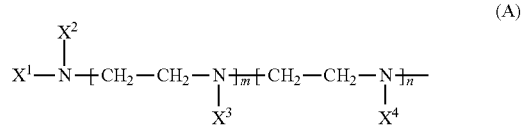

(wherein $X^1$, $X^2$, $X^3$, and $X^4$ independently represent hydrogen atom, an alkyl group which may have a substituent, or a protective group for amino group, and m and n independently represent 0 or 1), provided that $R^1$ and $R^2$ do not simultaneously represent hydrogen atom; $R^3$ and $R^4$ independently represent hydrogen atom, a $C_{1-6}$ alkyl group which may have a substituent, or a $C_{1-6}$ alkoxy group which may have a substituent; $R^5$, $R^6$, $R^7$, $R^8$, $R^9$, $R^{10}$, $R^{11}$, and $R^{12}$ independently represent hydrogen atom, sulfa group, phospho group, a halogen atom, or a $C_{1-6}$ alkyl group which may have a substituent; $R^{13}$ and $R^{14}$ independently represent a $C_{1-18}$ alkyl group which may have a substituent; $Z^1$ represents oxygen atom, sulfur atom, or —N(R$^{15}$)— (wherein R$^{15}$ represents hydrogen atom, or a C$_{1-6}$ alkyl group which may have a substituent); Y$^1$ and Y$^2$ independently represent —C(=O)—, —C(=S)—, or —C(R$^{16}$)(R$^{17}$) (wherein R$^{16}$ and R$^{17}$ independently represent a C$_{1-6}$ alkyl group which may have a substituent); and M$^-$ represents a counter ion in a number required for neutralizing the charge]. The compound (except for a compound wherein any one or more of X$^1$, X$^2$, X$^3$, and X$^4$ represent a protective group for amino group) is useful as a fluorescent probe for detecting a metal ion, nitrogen monoxide, and the like.

As a preferred compound falling within the scope of the aforementioned invention, there is provided a compound represented by the following general formula (IA):

[Formula 3]

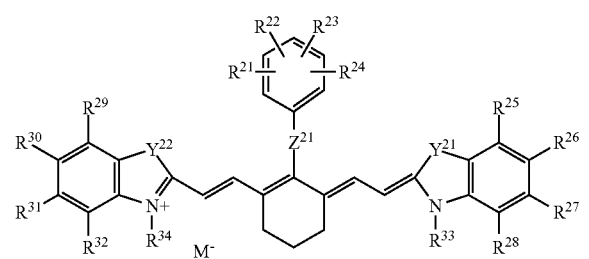

(IA)

[wherein R$^{21}$ and R$^{22}$ represent amino groups substituting at adjacent positions on the benzene ring, and one of the amino groups may have one alkyl group which may have a substituent; R$^{23}$ and R$^{24}$ independently represent hydrogen atom, a C$_{1-6}$ alkyl group which may have a substituent, or a C$_{1-6}$ alkoxy group which may have a substituent; R$^{25}$, R$^{26}$, R$^{27}$, R$^{28}$, R$^{29}$, R$^{30}$, R$^{31}$, and R$^{32}$ independently represent hydrogen atom, sulfo group, phospho group, a halogen atom, or a C$_{1-6}$ alkyl group which may have a substituent; R$^{33}$ and R$^{34}$ independently represent a C$_{1-18}$ alkyl group which may have a substituent; Z$^{21}$ represents oxygen atom, sulfur atom, or —N(R$^{35}$)— (wherein R$^{35}$ represents hydrogen atom, or a C$_{1-6}$ alkyl group which may have a substituent); Y$^{21}$ and Y$^{22}$ independently represent —C(=O)—, —C(=S)—, or —C(R$^{36}$)(R$^{37}$)— (wherein R$^{36}$ and R$^{37}$ independently represent a C$_{1-6}$ alkyl group which may have a substituent); and M$^-$ represents a counter ion in a number required for neutralizing the charge], and according to a preferred embodiment thereof, there is provided the aforementioned compound, wherein R$^{23}$, R$^{24}$, R$^{25}$, R$^{26}$, R$^{27}$, R$^{28}$, R$^{29}$, R$^{30}$, R$^{31}$, and R$^{32}$ are hydrogen atoms, R$^{33}$ and R$^{34}$ are C$_{1-6}$ alkyl groups substituted with sulfo group, Z$^{21}$ is oxygen atom, and Y$^{21}$ and Y$^{22}$ are —C(CH$_3$)$_2$—. As another aspect of the present invention, there is provided a reagent for measurement of nitrogen monoxide, which comprises a compound represented by the aforementioned general formula (IA).

The present invention also provides a compound represented by the following general formula (IB):

[Formula 4]

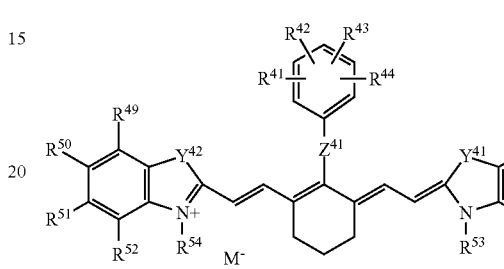

(IB)

[wherein R$^{41}$ and R$^{42}$ combine together to represent a group represented by —N=N—NR$^{58}$— which forms a ring at the adjacent positions on the benzene ring (wherein R$^{58}$ represents hydrogen atom, or a C$_{1-6}$ alkyl group which may have a substituent), or R$^{41}$ and R$^{42}$ represent a combination of an amino group (which may have a C$_{1-6}$ alkyl group which may have a substituent, or a protective group for amino group) and nitro group substituting at adjacent positions on the benzene ring; R$^{43}$ and R$^{44}$ independently represent hydrogen atom, a C$_{1-6}$ alkyl group which may have a substituent, or a C$_{1-6}$ alkoxy group which may have a substituent; R$^{45}$, R$^{46}$, R$^{47}$, R$^{48}$, R$^{49}$, R$^{50}$, R$^{51}$, and R$^{52}$ independently represent hydrogen atom, sulfo group, phospho group, a halogen atom, or a C$_{1-6}$ alkyl group which may have a substituent; R$^{53}$ and R$^{54}$ independently represent a C$_{1-18}$ alkyl group which may have a substituent; Z$^{41}$ represents oxygen atom, sulfur atom, or —N(R$^{55}$)— (wherein R$^{55}$ represents hydrogen atom, or a C$_{1-6}$ alkyl group which may have a substituent); Y$^{41}$ and Y$^{42}$ independently represent —C(=O)—, —C(=S)—, or —C(R$^{56}$)(R$^{57}$)— (wherein R$^{56}$ and R$^{57}$ independently represent a C$_{1-6}$ alkyl group which may have a substituent); and M$^-$ represents a counter ion in a number required for neutralizing the charge], and according to a preferred embodiment of this invention, there is provided the aforementioned compound, wherein R$^{43}$, R$^{44}$, R$^{45}$, R$^{46}$, R$^{47}$R$^{48}$, R$^{49}$R$^{50}$, R$^{51}$, and R$^{52}$ are hydrogen atoms, R$^{53}$ and R$^{54}$ are C$_{1-6}$ alkyl groups substituted with sulfo group, Z$^{41}$ is oxygen atom, and Y$^{41}$ and Y$^{42}$ are —C(CH$_3$)$_2$—.

From further aspects of the present invention, there are provided a method for measuring nitrogen monoxide, which comprises (a) the step of reacting a compound represented by the aforementioned general formula (IA) with nitrogen monoxide, and (b), the step of detecting a compound of the general formula (IB) [wherein R$^{41}$ and R$^{42}$ combine together to represent a group represented by —N=N—NR$^{58}$— which forms a ring at the adjacent positions on the benzene ring (wherein R$^{68}$ represents hydrogen atom, or a C$_{1-6}$ alkyl group which may have a substituent)] produced in the aforementioned step (a); and use of a compound represented by the aforementioned general formula (IA) as a reagent for measuring nitrogen monoxide.

The present invention also provides a compound represented by the following general formula (IC):

[Formula 5]

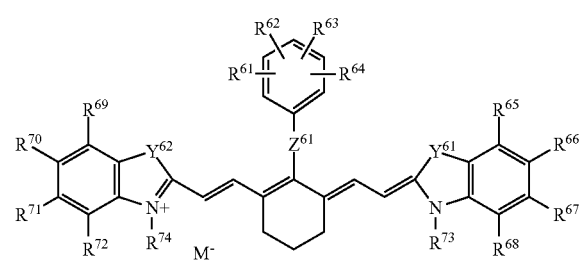

(IC)

[wherein $R^{61}$ and $R^{62}$ independently represent hydrogen atom, or a group represented by the following formula (B);

[Formula 6]

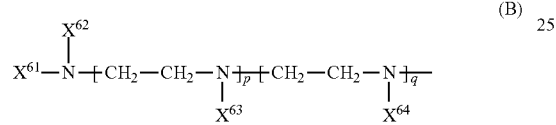

(B)

(wherein $X^{61}$, $X^{62}$, $X^{63}$, and $X^{64}$ independently represent hydrogen atom, an alkyl group which may have a substituent, or a protective group for amino group, and p and q independently represent 0 or 1), provided that $R^{61}$ and $R^{62}$ do not simultaneously represent hydrogen atom, and when $R^{61}$ and $R^{62}$ simultaneously represent a group represented by the formula (B), in at least one of the groups represented by the formula (B), either p or q, or both represent 1; $R^{63}$ and $R^{64}$ independently represent hydrogen atom, a $C_{1-6}$ alkyl group which may have a substituent, or a $C_{1-6}$ alkoxy group which may have a substituent; $R^{65}$, $R^{66}$, $R^{67}$, $R^{68}$, $R^{69}$, $R^{70}$, $R^{71}$, and $R^{72}$ independently represent hydrogen atom, sulfo group, phospho group, a halogen atom, or a $C_{1-6}$ alkyl group which may have a substituent; $R^{73}$ and $R^{74}$ independently represent a $C_{1-18}$ alkyl group which may have a substituent; $Z^{61}$ represents oxygen atom, sulfur atom, or —N($R^{75}$)— (wherein $R^{75}$ represents hydrogen atom, or a $C_{1-6}$ alkyl group which may have a substituent); $Y^{61}$ and $Y^{62}$ independently represent —C(=O)—, —C(=S)—, or —C($R^{76}$)($R^{77}$)— (wherein $R^{76}$ and $R^{77}$ independently represent a $C_{1-6}$ alkyl group which may have a substituent); and $M^-$ represents a counter ion in a number required for neutralizing the charge].

From further aspects of the present invention, there are provided a fluorescent probe for zinc containing a compound represented by the aforementioned general formula (IC) (except for a compound wherein any one or more of $X^{61}$, $X^{62}$, $X^{63}$, and $X^{64}$ are protective group for amino group); and a zinc complex formed from a compound represented by the aforementioned general formula (IC) (except for a compound wherein any one or more of $X^{61}$, $X^{62}$, $X^{63}$, and $X^{64}$ are protective group for amino group), and a zinc ion. This fluorescent probe for zinc can be used to measure zinc ions in a tissue or a cell.

From still further aspects of the present invention, there are provided a method of using a compound represented by the aforementioned general formula (IC) (except for a compound wherein any one or more of $X^{61}$, $X^{62}$, $X^{63}$, and $X^{64}$ are protective group for amino group) as a fluorescent probe for zinc; a method for measuring zinc ions, which comprises (a) the step of reacting a compound represented by the aforementioned general formula (IC) (except for a compound wherein any one or more of $X^{61}$, $X^{62}$, $X^{63}$, and $X^{64}$ are protective group for amino group) with a zinc ion, and (b) the step of measuring fluorescence intensity of a zinc complex produced in the aforementioned step (a); and use of a compound represented by the aforementioned general formula (IC) (except for a compound wherein any one or more of $X^{61}$, $X^{62}$, $X^{63}$, and $X^{64}$ are protective group for amino group) as a fluorescent probe for zinc.

Effect of the Invention

The compound of the present invention has a property of very efficiently reacting with nitrogen monoxide and a metal ion (zinc ion and the like) to give a fluorescence substance, and the fluorescence substance emits extremely intense fluorescence by excitation with light of the near-infrared region. Therefore, by using the compound as a fluorescent probe, it becomes possible to measure nitrogen monoxide or metal ions in a deep tissue of a living body.

BEST MODE FOR CARRYING OUT THE INVENTION

Figure 1:
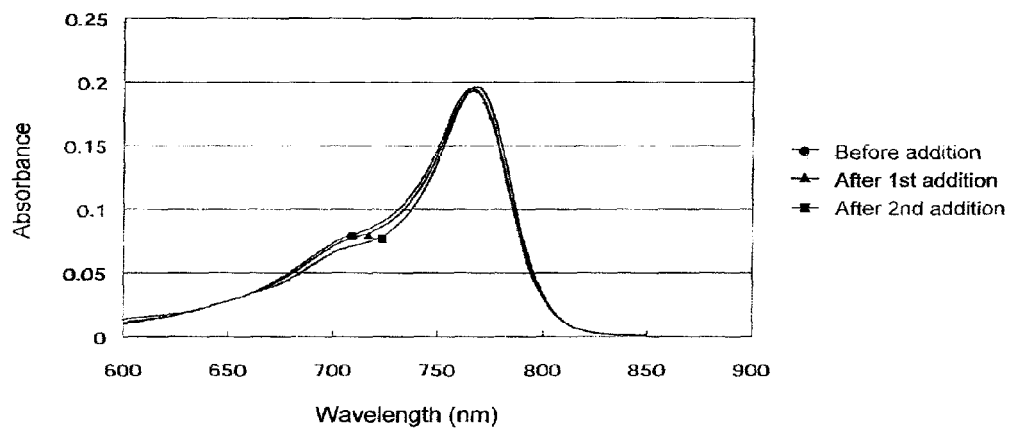
FIG. 1 shows change of absorption spectrum of the compound 2 caused by addition of nitrogen monoxide.

In the specification, the alkyl group may be a linear, branched, or cyclic alkyl group, or a combination thereof, unless otherwise specifically mentioned. An alkyl moiety of other substituents containing the alkyl moiety (e.g. alkoxy group) should also be understood in the same manner. Further, when "which may have a substituent" is referred to for a certain functional group, type, number, and substitution position of the substituent are not particularly limited. The functional group may have, for example, an alkyl group, an alkoxy group, an aryl group, a halogen atom (it may be any of fluorine atom, chlorine atom, bromine atom, and iodine atom), hydroxy group, amino group, carboxy group or an ester thereof, sulfo group or an ester thereof, or the like as the substituent. Further, when the aryl group is referred to in the specification, the group may be either a monocyclic or polycyclic aryl group. Phenyl group can be preferably used.

In the general formula (I), when $R^3$ and/or $R^4$ represent a $C_{1-6}$ alkyl group, or a $C_{1-6}$ alkoxy group, it is preferred that these groups bind at the 2- and 5-position on the benzene ring. When these groups exist, the quantum yield and reaction rate may be improved, and thus detection sensitivity may sometimes be increased. As the alkyl group represented by $R^3$ or $R^4$, methyl group is preferred, and methoxy group is preferred as the alkoxy group. It is also preferred that both $R^3$ and $R^4$ are hydrogen atoms. $R^{23}$ and $R^{24}$ in the general formula (IA), $R^{43}$ and $R^{44}$ in the general formula (IB), and $R^{63}$ and $R^{64}$ in the general formula (IC) should also be understood in the same manner.

$R^5$, $R^6$, $R^7$, $R^8$, $R^9$, $R^{10}$, $R^{11}$, and $R^{12}$ independently represent hydrogen atom, sulfo group, phospho group, a halogen atom, or a $C_{1-6}$ alkyl group which may have a substituent. As the $C_{1-6}$ alkyl group represented by $R^5$, $R^6$, $R^7$, $R^8$, $R^9$, $R^{10}$, $R^{11}$, or $R^{12}$, methyl group, ethyl group, and the like are preferred, and as the halogen atom represented by $R^5$, $R^6$, $R^7$, $R^8$, $R^9$, $R^{10}$, $R^{11}$, or $R^{12}$, fluorine atom, chlorine atom, and the like are preferred. The sulfo group and phospho group represented by $R^5$, $R^6$, $R^7$, $R^8$, $R^9$, $R^{10}$, $R^{11}$, or $R^{12}$ may form an ester. All of $R^5$, $R^6$, $R^7$, $R^8$, $R^9$, $R^{10}$, $R^{11}$, and $R^{12}$ may be hydrogen atoms. $R^{25}$, $R^{26}$, $R^{27}$, $R^{28}$, $R^{29}$, $R^{30}$, $R^{31}$ and $R^{32}$ in the general formula (IA), $R^{45}$, $R^{46}$, $R^{47}$, $R^{48}$, $R^{49}$, $R^{50}$, $R^{51}$, and $R^{52}$ in the general formula (IB), and $R^{65}$, $R^{66}$, $R^{67}$, $R^{68}$, $R^{69}$, $R^{70}$, $R^{71}$, and $R^{72}$ in the general formula (IC) should also be understood in the same manner as that for $R^5$, $R^6$, $R^7$, $R^8$, $R^9$, $R^{10}$, $R^{11}$, and $R^{12}$ mentioned above.

$R^{13}$ and $R^{14}$ independently represent a $C_{1-18}$ alkyl group which may have a substituent. Examples of the alkyl group include, for example, methyl group, ethyl group, n-propyl group, isopropyl group, n-butyl group, isobutyl group, sec-butyl group, tert-butyl group, n-pentyl group, isopentyl group, neopentyl group, tert-pentyl group, 1-methylbutyl group, 2-methylbutyl group, 1-ethylpropyl group, n-hexyl group, 1-methylpentyl group, 2-methylpentyl group, 3-methylpentyl group, 4-methylpentyl group, 2,3-dimethylbutyl group, 1,3-dimethylbutyl group, 1,2-dimethylbutyl group, 1-ethylbutyl group, 2-ethylbutyl group, 1-isopropylpropyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, and the like. As the alkyl group, a linear alkyl group is preferred. Examples of the substituent that can exist on the $C_{1-18}$ alkyl group represented by $R^{13}$ or $R^{14}$ include, for example, an alkoxy group, an aryl group, a halogen atom (it may be any of fluorine atom, chlorine atom, bromine atom, and iodine atom), hydroxy group, amino group, carboxy group or an ester thereof, sulfo group or an ester thereof, and the like. Among them, carboxy group, sulfo group, and the like are preferred. Both of $R^{13}$ and $R^{14}$ may be unsubstituted $C_{1-18}$ alkyl groups, and it is also preferred that one of the $C_{1-18}$ alkyl groups has a substituent. $R^{33}$ and $R^{34}$ in the general formula (IA), $R^{53}$ and $R^{54}$ in the general formula (IB), and $R^{73}$ and $R^{74}$ in the general formula (IC) should also be understood in the same manner as that for $R^{13}$ and $R^{14}$ mentioned above.

$Z^1$ represents oxygen atom, sulfur atom, or $-N(R^{15})-$ wherein $R^{15}$ represents hydrogen atom, or a $C_{1-6}$ alkyl group which may have a substituent. It is preferred that $Z^1$ is oxygen atom. As $R^{15}$, hydrogen atom, methyl group, and the like are preferred. $Y^1$ and $Y^2$ independently represent $-C(=O)-$, $-C(=S)-$, or $-C(R^{16})(R^{17})-$, and $R^{16}$ and $R^{17}$ independently represent a $C_{1-6}$ alkyl group which may have a substituent. It is preferred that $Y^1$ and $Y^2$ are $-C(R^{16})(R^{17})-$, and as $R^{16}$ and $R^{17}$, methyl group is preferred. $Z^{21}$, $R^{35}$, $Y^{21}$, $Y^{22}$, $R^{36}$ and $R^{37}$ in the general formula (IA), $Z^{41}$, $R^{55}$, $Y^{41}$, $Y^{42}$, $R^{56}$, and $R^{57}$ in the general formula (IB), and $Z^{61}$, $R^{75}$, $Y^{61}$, $Y^{62}$, $R^{76}$, and $R^{77}$ in the general formula (IC) should also be understood in the same manner as that for $Z^1$, $R^{15}$, $Y^1$, $Y^2$, $R^{16}$, and $R^{17}$ mentioned above. $M^-$ represents a counter ion in a number required for neutralizing the charge. Examples of the counter ion include, for example, metal ions such as sodium ion, potassium ion and magnesium ion, quaternary ammonium ions, ions of amino acids such as glycine, and the like. For example, when carboxy group, sulfo group or the like exists on the $C_{1-18}$ alkyl groups represented by $R^{13}$ and $R^{14}$ in the general formula (I), or when one or more of $R^5$, $R^6$, $R^7$, $R^8$, $R^9$, $R^{10}$, $R^{11}$, and $R^{12}$ represent sulfo group or phospho group, and sodium ion is used as the counter ion, two or more counter ions may be needed as $M^-$. Further, when one carboxy group or sulfo group exists on one of the $C_{1-18}$ alkyl groups represented by $R^{13}$ and $R^{14}$ in the general formula (I), the positive charge of the quaternary nitrogen atom to which $R^{14}$ binds and the anion of the carboxy group or sulfo group form an intramolecular zwitterion, and therefore the counter ion required for neutralizing the charge may become unnecessary.

Examples of the alkyl group represented by $X^1$, $X^2$, $X^3$, or $X^4$ in the group represented by the formula (A) in the general formula (I) include, for example, a linear or branched $C_{1-18}$ alkyl group (preferably $C_{1-6}$ alkyl group). The alkyl group may have a substituent. Type, number and substitution position of the substituent on the alkyl group are not particularly limited, and examples of the substituent include, for example, a halogen atom, amino group, hydroxy group, an aryl group, a heteroaryl group, and the like. However, the substituent on the alkyl group is not limited to these. As the substituent on the alkyl group, 2-pyridyl group can be preferably exemplified, and in such a case, it is preferred that the alkyl group is methyl group.

Type of the protective group for amino group represented by $X^1$, $X^2$, $X^3$, or $X^4$ is not particularly limited. For example, p-nitrobenzenesulfonyl group, trifluoroacetyl group, trialkylsilyl group, and the like can be suitably used. As for the protective group for amino group, for example, "Protective Groups in Organic Synthesis," T. W. Greene, John Wiley & Sons, Inc. (1981), and the like can be referred to.

As for the compound represented by the general formula (I), it is preferred that both $R^1$ and $R^2$ are groups represented by the formula (A), and m and n represent 0 in each of the groups represented by the formula (A), and in the above compounds, it is preferred that both $X^1$ and $X^2$ are hydrogen atoms. Further, in the compounds as mentioned above, it is preferred that both $X^1$ and $X^2$ are hydrogen atoms in one of the groups represented by the formula (A), and $X^1$ is hydrogen atom, and $X^2$ is an alkyl group (for example, methyl group) in the other group represented by the formula (A). Further, when both $R^1$ and $R^2$ represent a group represented by the formula (A), and one of m or n or both of them represent 1 in at least one of the groups represented by the formula (A) in the compound represented by the general formula (I), or when one of $R^1$ and $R^2$ represents hydrogen atom, and the other represents a group represented by the formula (A) in the compound represented by the general formula (I), it is preferred that four of the groups $X^1$ to $X^4$, preferably $X^1$ and $X^2$, are 2-pyridylmethyl groups in the group represented by the formula (A). In this embodiment, as for the compound represented by the aforementioned general formula (I), it is preferred that m is 0, n is 1, and $X^4$ is hydrogen atom, and in the above compounds, it is still more preferred that both $X^1$ and $X^2$ are 2-pyridylmethyl groups.

In the aforementioned general formula (IA), $R^{21}$ and $R^{22}$ represent amino groups substituted at adjacent positions on the benzene ring. Although both $R^{21}$ and $R^{22}$ may be unsubstituted amino groups, either $R^{21}$ or $R^{22}$ may be substituted with one alkyl group, and the alkyl group may have one or more substituents. Examples of the alkyl group that substitutes on the amino group include, for example, a linear or branched $C_{1-18}$ alkyl group (preferably $C_{1-6}$ alkyl group), and specifically, for example, methyl group, ethyl group, n-propyl group, isopropyl group, n-butyl group, sec-butyl group, tert-butyl group, and the like can be used. Examples of the alkyl group which has a substituent include, for example, a $C_{1-6}$ alkyl group substituted with a substituted or unsubstituted aryl group (aralkyl group), and the like. As the aryl-substituted alkyl group, for example, benzyl group, phenethyl group, para-methoxybenzyl group, para-ethoxycarbonylbenzyl group, para-carboxybenzyl group, and the like can be used.

In the aforementioned general formula (IB), $R^{41}$ and $R^{42}$ combine together to represent a —N=N—NR$^{58}$— group which forms a ring at adjacent positions on the benzene ring. $R^{58}$ represents hydrogen atom, or an alkyl group which may have a substituent. Examples of the alkyl group include a linear or branched $C_{1-18}$ alkyl group (preferably $C_{1-6}$ alkyl group), and examples of the alkyl group which has a substituent include, for example, a substituted or unsubstituted aralkyl group. As the aralkyl group, benzyl group, phenethyl group, para-methoxybenzyl group, para-ethoxycarbonylbenzyl group, para-carboxybenzyl group, and the like can be used, for example.

$R^{41}$ and $R^{42}$ also represent a combination of an amino group (which may have one substituent) and nitro group, which substitute at adjacent positions on the benzene ring, wherein either one of $R^{41}$ and $R^{42}$ represents an amino group, and the other represents nitro group. Although the amino group represented by one of $R^{41}$ and $R^{42}$ may be unsubstituted, said group may have one alkyl group, for example, $C_{1-18}$ alkyl group, preferably $C_{1-6}$ alkyl group. The alkyl group may have a substituent. For example, a substituted or unsubstituted aralkyl group may substitute on the amino group. Further, the amino group may have a protective group for amino group, for example, an acyl group such as acetyl group, trifluoroacetyl group, and benzoyl group; an alkylsilyl group such as trimethylsilyl group, or the like. An aralkyl group such as benzyl group may also be used as the protective group.

In the group represented by the formula (B) in the general formula (IC), $X^{61}$, $X^{62}$, $X^{63}$, and $X^{64}$ independently represent hydrogen atom, an alkyl group which may have a substituent, or a protective group for amino group, and p and q independently represent 0 or 1. The alkyl group which may have a substituent and the protective group for amino group represented by $X^{61}$, $X^{62}$, $X^{63}$, and $X^{64}$ should be understood in the same manner as that for those explained for $X^1$, $X^2$, $X^3$, and $X^4$. When both of $R^{61}$ and $R^{62}$ represent a group represented by the formula (B), either p or q, or both of them represents 1 in at least one of the groups represented by the formula (B). As for the compound represented by the aforementioned general formula (IC), it is preferred that one of $R^{61}$ and $R^{62}$ represents hydrogen atom, and the other represents a group represented by the formula (B). As for the group represented by the formula (B), it is preferred that four of the groups, $X^{61}$ to $X^{64}$, preferably $X^{61}$ and $X^{62}$, are 2-pyridylmethyl groups. As for the compound represented by the aforementioned general formula (IC), it is preferred that p is 0, q is 1, and $X^{64}$ is hydrogen atom, and in such a case, it is preferred that both $X^{61}$ and $X^{62}$ are 2-pyridylmethyl groups.

The compound of the present invention represented by the aforementioned general formula (I), (IA), (IB), or (IC) may have one or more asymmetric carbons. Any of optical isomers in an optically pure form, arbitrary mixtures of optical isomers, racemates, diastereoisomers in a pure form, mixtures of diastereoisomers, and the like based on one or more asymmetric carbon atoms fall within the scope of the present invention. The compound of the present invention may exist as a hydrate or solvate, and it should be understood that these substances also fall within the scope of the present invention.

Preparation examples are shown in the scheme mentioned below for a compound of the formula (IA) wherein $R^{23}$, $R^{24}$, $R^{25}$, $R^{26}$, $R^{27}$, $R^{28}$, $R^{29}$, $R^{30}$, $R^{31}$, and $R^{32}$ are hydrogen atoms, $R^{33}$ and $R^{34}$ are n-propyl groups having one sulfo group, $Z^{21}$ is oxygen atom, $Y^{21}$ and $Y^{22}$ are —C(CH$_3$)$_2$—, and M$^-$ is one sodium ion, and a compound of the formula (IB) wherein $R^{43}$, $R^{44}$, $R^{45}$, $R^{46}$, $R^{47}$, $R^{48}$, $R^{49}$, $R^{50}$, $R^{51}$, and $R^{52}$ are hydrogen $Y^{41}$ atoms, $R^{53}$ and $R^{54}$ are n-propyl group having one sulfo group, $Z^{41}$ is oxygen atom, and $Y^{42}$ are —C(CH$_3$)$_2$—, and M$^-$ is one sodium ion as typical examples of the compound represented by the aforementioned general formula (IA), and the compound represented by the general formula (IB) (wherein $R^{41}$ and $R^{42}$ represent a combination of an amino group and nitro group which substitute at adjacent positions on the benzene ring). Details of each of the synthetic steps are specifically explained in the examples of the specification. Further, the compound represented by the general formula (IB) wherein $R^{41}$ and $R^{42}$ combine together to represent the —N=N—NR$^{58}$— group which forms a ring at adjacent positions on the benzene ring can be prepared by reacting a compound represented by the aforementioned general formula (IA) and nitrogen monoxide. These compounds have intense fluorescence as described later, and are useful for measurement of nitrogen monoxide.

[Formula 7]

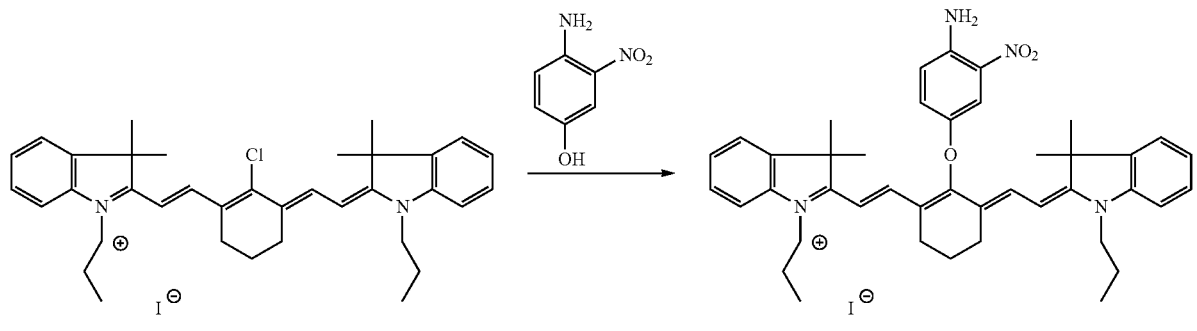

Compound A

1

-continued
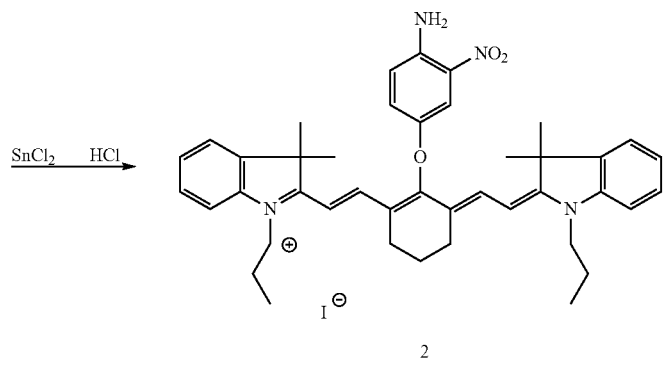
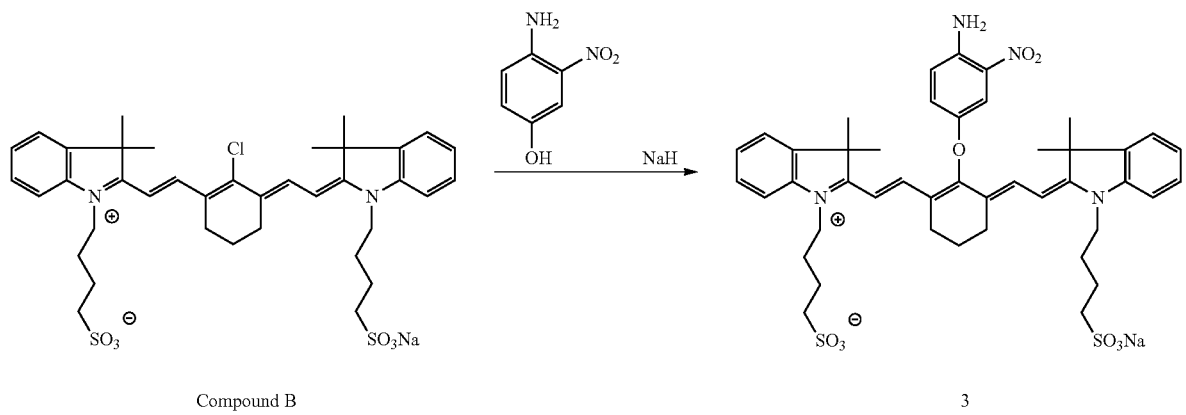
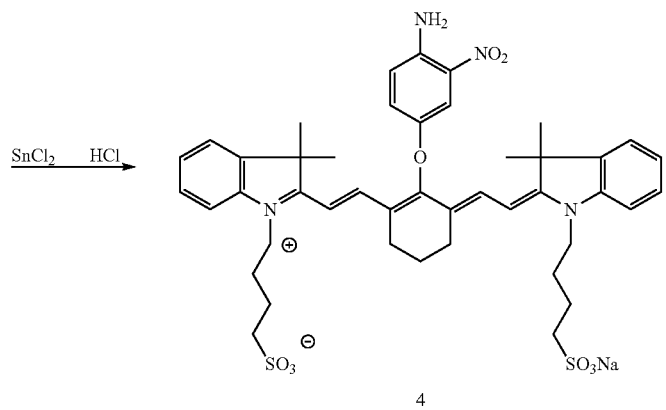
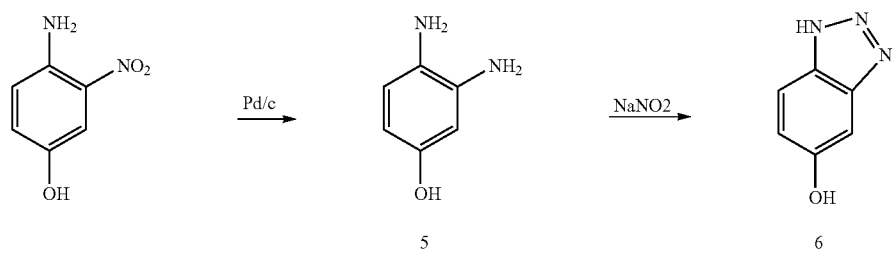

-continued

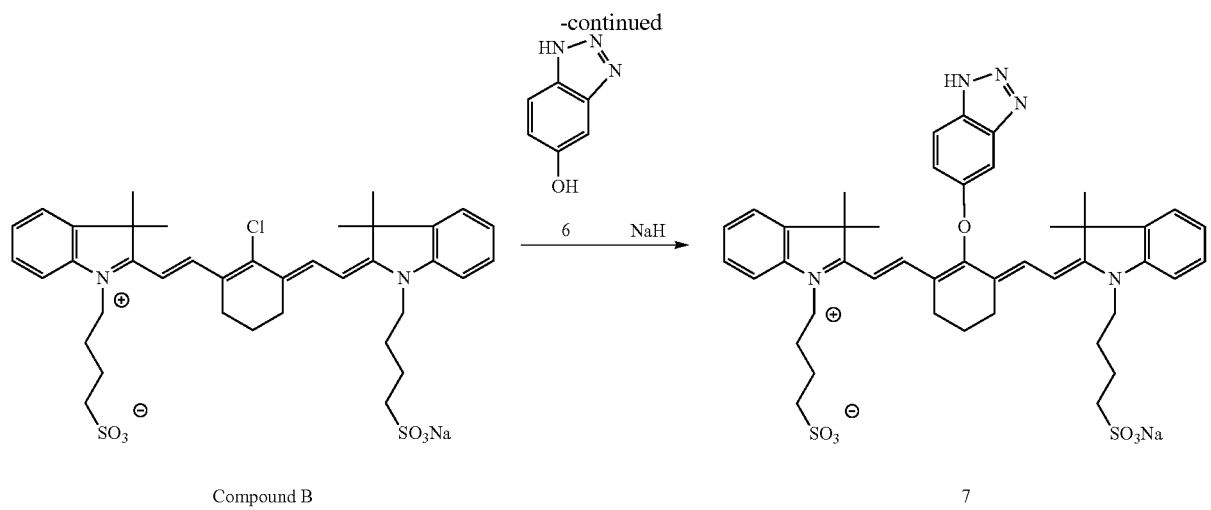

It will be understood by those skilled in the art that the compounds falling within the scopes of the general formulas (IA) and (IB) can be easily produced by referring to the general explanations for the aforementioned scheme, and specific explanations in the examples. Moreover, the preparation methods for the compounds having a group represented by the formula (B) are specifically explained in detail in International Patent Publication WO01/62755, and therefore those skilled in the art can easily prepare the compounds represented by the general formula (IC) by preparing a phenol derivative having a group represented by the formula (B) with referring to the aforementioned publication, and reacting the phenol derivative with a cyanine compound according to the method shown in the aforementioned scheme.

The compounds represented by the formula (IA) of the present invention have a property that they efficiently react with nitrogen monoxide under a neutral condition and provide compounds of the formula (IB) (wherein $R^{41}$ and $R^{42}$ combine together to form the group —N=N—$NR^{58}$— which forms a ring at adjacent positions on the benzene ring) in a good yield. The compounds represented by the formula (IA), per se, emit almost no fluorescence when irradiated with excitation light of around 650 to 900 nm under a neutral condition, whereas the compounds of the above formula (IB) have the property of emitting extremely strong fluorescence under the same condition. Therefore, nitrogen monoxide in living tissues or cells can be measured by introducing the compound represented by the formula (IA) into a living tissue or a cell to allow the compound to react with nitrogen monoxide to form the fluorescent compound of the above formula (IB), and measuring the fluorescence of the compound. In particular, the compounds of the formula (IA) of the present invention have superior reactivity with nitrogen monoxide, and the compounds of the formula (IB) emit extremely intense fluorescence with an excitation light of the near-infrared region, which has high tissue permeability. Therefore, they have a superior characteristic that they enable measurement of nitrogen monoxide in a deep tissue of a living body with high sensitivity and accuracy.

Therefore, the method for measuring nitrogen monoxide provided by the present invention comprises the steps of reacting a compound represented by the general formula (IA) with nitrogen monoxide to generate a compound of the general formula (IB), and measuring fluorescence of the compound of the general formula (IB) (wherein $R^{41}$ and $R^{42}$ combine together to represent the —N=N—$NR^{58}$— group which forms a ring at adjacent positions on the benzene ring). The term "measurement" used in the specification should be construed in its broadest sense, which includes various measurement purposes such as, for example, detection, quantification, qualitative analysis and the like. The above reaction can preferably be carried out under a neutral condition, for example, in the range of from pH 6.0 to 8.0, preferably in the range of from pH 6.5 to 7.8, and more preferably in the range of from pH 6.8 to 7.6. However, the measurement of nitrogen monoxide using the compounds of the present invention is not limited to the measurements under the neutral range or weakly acidic range. For example, measurement can also be performed under a strongly acidic condition such as in gastric mucosal cells.

The measurement of fluorescence can be carried out according to a known fluorometry method (see, for example, Wiersma, J. H., Anal. Lett., 3, pp. 123-132, 1970; Sawicki, C. R., Anal. Lett., 4, pp. 761-775, 1971; Damiani, P. and Burini, G., Talanta, 8, pp. 649-652, 1986; Misko, T. P., Anal. Biochem., 214, pp. 11-16, 1993, etc.). For the nitrogen monoxide measurement according to the present invention, for example, irradiation with light of about 650 to 900 nm as excitation light, and measurement of fluorescence of about 800 nm may preferably be performed. If lights having such a wavelength is used, the excitation light transmits living tissues without being attenuated and reaches tissues in a deep position, and thus highly sensitive measurement becomes possible at that position.

Where particularly highly sensitive measurement is required, the aforementioned measurement of nitrogen monoxide may be carried out in the presence of an oxygen source. As the oxygen source, for example, oxygen, ozone, oxide compounds or other can be used. As the oxygen, dissolved oxygen can generally be used, and if desired, oxygen gas may be introduced into the reaction system, or an agent that can generate oxygen (e.g., hydrogen peroxide) may be added. The oxide compounds are not particularly limited so long as they have an oxide bond that can easily be cleaved, e.g., N—O, S—O, or P—O. For example, PTIO (2-phenyl-4,4,5,5-tetramethylimidazoline-1-oxyl-3-oxide, Maeda, H., et al., J. Leuk. Biot, 56, pp. 588-592, 1994; and Akaike, T., et al., Biochemistry, 32, pp. 827-832, 1993) or derivatives thereof (carboxy-PTIO which has carboxy group introduced at the para-position of the phenyl group of PTIO etc.), triphenylphosphine oxide, triethylamine oxide or the like can be used.

Among the oxide compounds mentioned above, PTIO and derivatives thereof carboxy-PTIO) are particularly preferred compounds, and they can be readily obtained by those skilled in the art (listed in, for example, Organic Chemicals Catalog, 32, 1994, Tokyo Kasei Co., Ltd. etc.). The oxide compounds, per se, may be used as a reaction agent, or those encapsulated in liposomes or other may also be used. Although the amount of the oxygen source is not particularly limited, preferable amount may be at least 1 μmol or more, preferably 10 to 30 μmol, more preferably about 10 to 20 μmol, based on nitrogen monoxide to be measured. From about 10 to 20 μmol of the oxide compound may preferably be added to samples for the measurement of a sample from a living body. However, a required amount of the oxygen source is generally supplied by dissolved oxygen. If the amount of oxygen source is extremely small, measuring sensitivity may sometimes be lowered, and if an extremely large amount of oxygen source exists, emission of fluorescence may be disadvantageously affected. Therefore, it is preferred that an amount of nitrogen monoxide to be measured is predicted by a preliminary experiment or a known method so that the oxygen source within an appropriate concentration range can be added. The reaction can be carried out at a temperature of from 10 to 25° C. In addition, the method for measurement of nitrogen monoxide by using a fluorescent probe is described in detail in Japanese Patent No. 3200024, and the like, and therefore those skilled in the art can measure nitrogen monoxide with high sensitivity by using the compounds of the present invention with referring to the aforementioned publication.

Further, the compounds of the present invention represented by the aforementioned general formula (IC) (except for a compound having a protective group for amino group) are useful as a fluorescent probe for zinc. Although the compounds of the present invention represented by the aforementioned general formula (IC), per se, do not have a property of emitting intense fluorescence, if they trap a zinc ion to form a zinc complex, they come to emit intense fluorescence. The aforementioned compounds have a characteristic that they can specifically trap a zinc ion, and very quickly form a complex. Further, the formed zinc complex has a characteristic that it emits intense fluorescence with a excitation light of the near-infrared region, which exhibits superior transmission through tissues of a living body. Therefore, the compounds of the present invention represented by the aforementioned general formula (IC) are extremely useful as fluorescent probes for zinc for measuring zinc ions in living cells and tissues, in particular, deep tissues, under a physiological condition.

The method for using the fluorescent probe for zinc according to the present invention is not particularly limited, and the probe can be used in the same manner as conventional zinc probes. In general, a substance selected from the group consisting of the compounds represented by the general formula (IC) and salts thereof is dissolved in an aqueous medium such as physiological saline or a buffered solution, or in a mixture of an aqueous medium and a water-miscible organic solvent such as ethanol, acetone, ethylene glycol, dimethylsulfoxide, and dimethylformamide, then the resultant solution is added to a suitable buffered solution containing cells or tissues, and a fluorescence spectrum can be measured. The fluorescent probe for zinc of the present invention may be combined with an appropriate additive and used in the form of a composition. For example, the probe may be combined with additives such as buffers, dissolving aids, and pH modifiers.

EXAMPLES

The present invention will be more specifically explained with reference to examples. However, the scope of the present invention is not limited to these examples. The compound numbers in the following examples correspond to those used in the above scheme.

Example 1

Synthesis of Compound 1

4-Amino-3-nitrophenol (39 mg, 0.25 mmol) and sodium hydride (60% in mineral oil, 10 mg, 0.25 mmol) were dissolved in dimethylformamide (DMF, 7 ml), and the solution was stirred at room temperature for 10 minutes under an argon atmosphere. During the stirring, the compound A (67 mg, 0.10 mmol) was dissolved in DMF (2 ml), this solution was added to the above solution, and the mixture was stirred at room temperature for 4 hours under an argon atmosphere. The product was purified by silica gel chromatography to obtain deep green solid (yield: 70%).

$^1$H NMR (CDCl$_3$ 300 MHz); δ 1.05 (t, 6H, J=7.3 Hz), 1.42 (s, 12H), 1.87 (m, 4H), 2.04 (m, 2H), 2.68 (t, 4H, J=5.0 Hz), 3.99 (t, 4H, J=7.2 Hz), 5.99 (d, 2H, J=14.4 Hz), 6.90 (s, 2H), 7.05-7.40 (m, 9H), 7.66-7.72 (m, 2H), 7.92 (d, 2H, J=14.4 Hz)

MS (FAB); 657 (M−I$^-$)

Synthesis of compound 2

The compound 1 (44 mg, 0.055 mmol) was dissolved in methanol (2 ml), concentrated hydrochloric acid (0.3 ml) and then tin chloride dihydrate (250 mg, 1.1 mmol) were added to the solution, and the mixture was stirred at 40° C. for 13 hours under an argon atmosphere. The reaction mixture was returned to room temperature, and then aqueous sodium hydroxide was added until pH of the mixture became 4, and then the reaction solution was evaporated under reduced pressure. The resulting mixture was dissolved in about 5 ml of methanol, and the solution was filtered and then evaporated under reduced pressure. The residue was purified by silica gel chromatography to obtain deep green solid (yield: 20%).

$^1$H NMR (CD$_3$OD 300 MHz); δ 0.92 (t, 6H, J=7.4 Hz), 1.31 (s, 12H), 1.74 (m, 4H), 1.92 (m, 2H), 2.61 (t, 4H, J=6.0 Hz), 3.96 (t, 4H, J=7.4 Hz), 6.02 (d, 211, J=14.1 Hz), 6.20 (dd, 1H, J=8.4, 2.8 Hz), 6.45 (d, H, J=2.8 Hz), 6.58 (d, 1H, J=8.54 Hz), 7.08-7.15 (m, 4H), 7.24-7.30 (m, 4H), 7.98 (d, 2H, J=14.1 Hz)

MS (FAB); 627 (M−I$^-$)

Synthesis of Compound 3

4-Amino-3-nitrophenol (93 mg, 0.60 mmol) and sodium hydride (60% in mineral oil, 24 mg, 0.60 mmol) were dissolved in DMF (16 ml), and the solution was stirred at room temperature for 10 minutes under an argon atmosphere. During the stirring, the compound B (180 mg, 0.24 mmol) was dissolved in DMF (5 ml), this solution was added to the above solution, and the mixture was stirred at room temperature for 4 hours under an argon atmosphere. The product was purified by silica gel chromatography to obtain deep green solid (yield: 80%).

$^1$H NMR (CD$_3$OD 300 MHz); δ 1.33 (s, 12H), 1.80-1.96 (m, 10H), 2.67 (t, 4H, J=5.9 Hz), 2.78 (t, 4H, J=7.0 Hz), 4.04

(t, 4H, J=6.3 Hz), 6.12 (d, 2H, J=14.3 Hz), 6.97 (d, 1H, J=9.3 Hz), 7.08-7.31 (m, 9H), 7.61 (d, 1H, J=2.9 Hz), 7.89 (d, 2H, J=14.3 Hz)

MS (FAB); 845 (M–Na$^+$+2H$^+$), 867 (M+H$^+$), 889 (M+Na$^+$)

Synthesis of Compound 4

The compound 3 (100 mg, 0.12 mmol) was dissolved in methanol (4 ml), concentrated hydrochloric acid (0.6 ml) and then tin chloride dihydrate (450 mg, 2.0 mmol) were added to the solution, and the mixture was stirred at 40° C. for 13 hours under an argon atmosphere. The reaction mixture was returned to room temperature, then aqueous sodium hydroxide was added until pH of the mixture became 7, and filtered, and then the reaction solution was evaporated under reduced pressure. The resulting mixture was dissolved in about 10 ml of methanol, and the solution was similarly filtered, and then evaporated under reduced pressure. The residue was purified by silica gel chromatography to obtain deep green solid (yield: 20%).

$^1$H NMR (CD$_3$OD 300 MHz); δ 1.30 (s, 12H), 1.82-1.92 (m, 10H), 2.62 (t, 4H, J=5.8 Hz), 2.77 (t, 4H, J=6.7 Hz), 4.01 (t, 4H, J=5.5 Hz), 6.05 (d, 2H, J=14.2 Hz), 6.19 (dd, 1H, J=8.4, 2.9 Hz), 6.45 (d, 1H, J=2.9 Hz), 6.58 (d, 1H, J=8.4 Hz), 7.06-7.28 (m, 8H), 7.97 (d, 2H, J=14.2 Hz)

MS (FAB); 815 (M–Na$^+$+2H$^+$), 837 (M+H$^+$), 859 (M+Na$^+$)

Synthesis of Compound 5

4-Amino-3-nitrophenol (2.0 g, 13 mmol) was dissolved in methanol (100 ml), 10% palladium/carbon catalyst (0.69 gm 0.65 mmol) was added portionwise to the solution. The mixture was stirred at room temperature for 3 hours under a hydrogen gas, and then the catalyst was removed by filtration. The filtrate was evaporated under reduced pressure to obtain black solid (yield: 92%)

$^1$H NMR (CD$_3$OD 300 MHz); δ 6.07 (dd, 1H, J=8.2, 2.7 Hz), 6.23 (d, 1H, J=2.7 Hz), 6.56 (d, 1H, J=8.2 Hz)

MS (EI); 124 (M$^+$)

Synthesis of Compound 6

The compound 5 (500 mg, 4.0 mmol) was dissolved in 0.2 N aqueous hydrochloric acid (150 ml), and sodium nitrite (280 mg, 4.0 mmol) was added portionwise to the solution with stirring at 0° C. The mixture, was stirred at room temperature for 1.5 hours, and then aqueous sodium hydroxide was added until pH of the mixture became 3. The reaction mixture was extracted with an appropriate volume of ethyl acetate, and then the organic phase was dried over anhydrous sodium sulfate. The solvent was evaporated under reduced pressure to obtain brown solid (yield: 80%).

$^1$H NMR (CD$_3$OD 300 MHz); δ 6.88 (m, 2H), 7.64 (d, 1H, J=9.7 Hz)

MS (ED; 135 (M$^+$)

Synthesis of Compound 7

The compound 6 (34 mg, 0.25 mmol) and sodium hydride (50% in mineral oil, 10 mg, 0.25 mmol) were dissolved in DMF (7 ml), and the solution was stirred at room temperature for 10 minutes under an argon atmosphere. During the stirring, the compound B (74 mg, 0.10 mmol) was dissolved in DMF (2 ml), this solution was added to the above solution, and the mixture was stirred at room temperature for 6 hours under an argon atmosphere. The product was roughly purified by silica gel chromatography, and then the crude product was purified by high performance liquid chromatography to obtain green solid (yield: 40%).

$^1$H NMR (DMSO-d$_6$ 300 MHz); δ 1.17 (s, 12H), 1.70-1.97 (m, 8H), 2.48 (m, 4H), 2.76 (t, 4H, J=6.0 Hz), 4.12 (t, 4H, J=6.6 Hz), 6.25 (d, 2H, J=14.2 Hz), 7.13-7.48 (m, 10H), 7.81 (d, 2H, J=14.2 Hz), 8.06 (d, 1H, J=9.0 Hz)

MS (FAB); 826 (M–Na$^+$+2H$^+$), 848 (M+H$^+$), 870 (M+Na$^+$)

Example 2

Confirmation of Generation of Triazole Compound by Addition of Nitrogen Monoxide The analysis conditions for HPLC were the same for all the measurements, i.e., an ODS column was used, and a solvent gradient of A/B=50/50 to 0/100 was used, wherein the solvent A was 0.1% TFA in water, and the solvent B was 0.1% TFA and 20% water in acetonitrile. The compound 4 was dissolved in 0.1 mM phosphate buffer, pH 7.4 and analyzed by HPLC. As a result, the retention time was 2.4 minutes. To this solution was added portionwise 0.1 mM phosphate buffer, pH 7.4, bubbled previously with nitrogen monoxide gas, and the solution was analyzed by HPLC after addition of each portion. As a result, it was observed that the peak at the retention time of 2.4 minutes lowered, and a peak at a retention time of 3.4 minutes newly emerged. Separately, a synthesized sample of the compound 7 as a triazole compound was dissolved in 0.1 mM phosphate buffer, pH 7.4 and analyzed by HPLC. As a result, the retention time was 3.4 minutes, which was consistent with the retention time of the peak newly appeared in the previous measurement. From the results described above, it was confirmed that the compound 4 reacted with nitrogen monoxide to generate the compound 7 as a triazole compound.

Example 3

Figure 2:
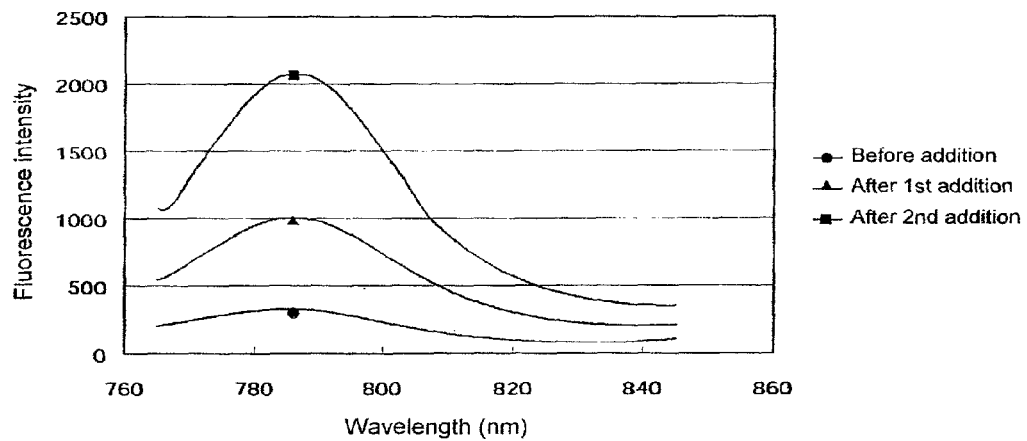
FIG. 2 shows change of fluorescence spectrum of the compound 2 caused by addition of nitrogen monoxide.

Change in Fluorescence Spectrum of Compound 2 Caused by Addition of Nitrogen Monoxide The compound 2 was dissolved in an appropriate volume of methanol to prepare a solution showing an absorbance of 0.2 at the absorption maximum wavelength (766 nm). Methanol bubbled with nitrogen monoxide gas was separately prepared beforehand, and added to the above solution 2 times in a small volume. Absorption spectrum and fluorescence spectrum of the solution was measured before the addition, after the first addition, and after the second addition. The change of the absorption spectrum is shown in FIG. 1. The absorption spectrum was hardly influenced by nitrogen monoxide. The change of the fluorescence spectrum is shown in FIG. 2. Although the maximum fluorescence wavelength observed by excitation with a light of 765 nm was 786 nm at all the measurement points, the fluorescence intensity, which was 330 before the addition of nitrogen monoxide, increased even to 1000 after the first addition, and to 2100 after the second addition. In other words, the fluorescence intensity of the triazole compound generated from the compound 2 by the reaction with nitrogen monoxide was found to increase at least 6.4 times at the maximum fluorescence wavelength.

Example 4

Figure 3:
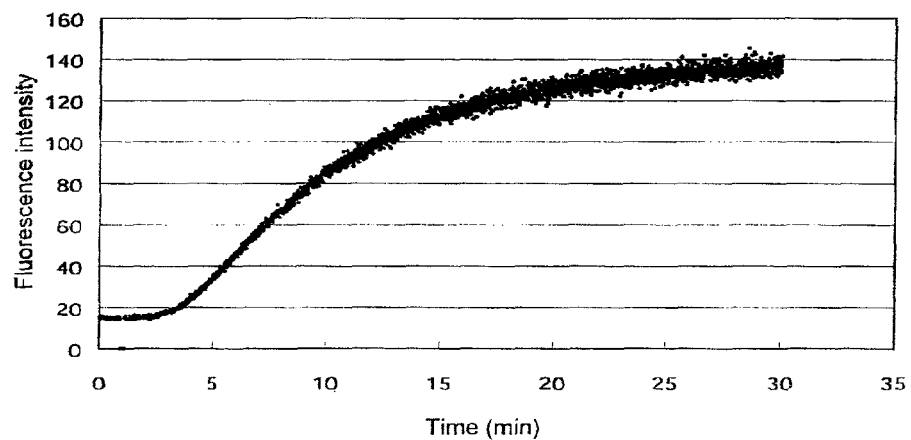
FIG. 3 shows change of fluorescence intensity of the compound 4 caused by addition of a nitrogen monoxide donor.

Change in Fluorescence Intensity of Compound 4 Caused by Addition of Nitrogen Monoxide Donor Among NOCs (Hrabie, J. A., J. Org. Chem., 58, pp. 1472-1476, 1993), which are spontaneous nitrogen monoxide releasers, NOC-13 (half-life is 13.7 minutes at 22° C. in 0.1 M phosphate buffer, pH 7.4) was used as a source for supplying nitrogen monoxide, and nitrogen monoxide generated in the reaction mixture was reacted with the compound 4. By using 10 mM phosphate buffer, pH 7.4 as a reaction solvent and adjusting both the concentrations of the compound 4 and NOC-13 to 5 µM, temporal change in fluorescence intensity was measured at 37° C. The results are shown in FIG. 3. The measurement was performed with an excitation wavelength of 765 nm and for a fluorescence wavelength of 790 nm. At the time point indicated as "1 minute" in the drawing, a stock solution of NOC-13 was added. The temporal increase of the fluorescence intensity indicates that a triazole compound was generated from the compound 4 depending on the amount of generated nitrogen monoxide.

Example 5

Application of Compound 2 to Observation of Deep Tissues in Living Body

In order to confirm that the compound 2 can trap nitrogen monoxide even in living tissues and can be observed from the outside, inside of an extracted rat kidney was stained by perfusion of the fluorescent probe through the vessels, and change in fluorescence intensity inside the kidney was observed by using a stereoscopic fluorescence microscope from the outside of the kidney.

Figure 4:
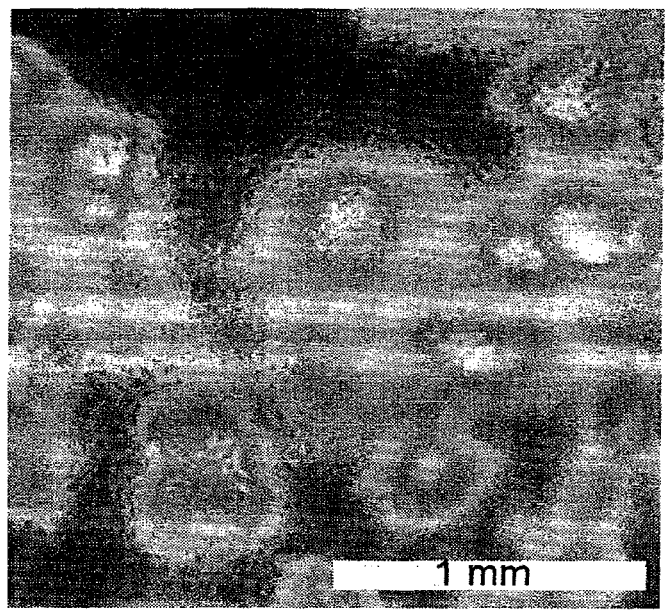
FIG. 4 shows a near-infrared fluorescence image of inside of kidney taken from the outside of the kidney, in which load of the compound 2 on the inside of the kidney can be confirmed.
Figure 5:
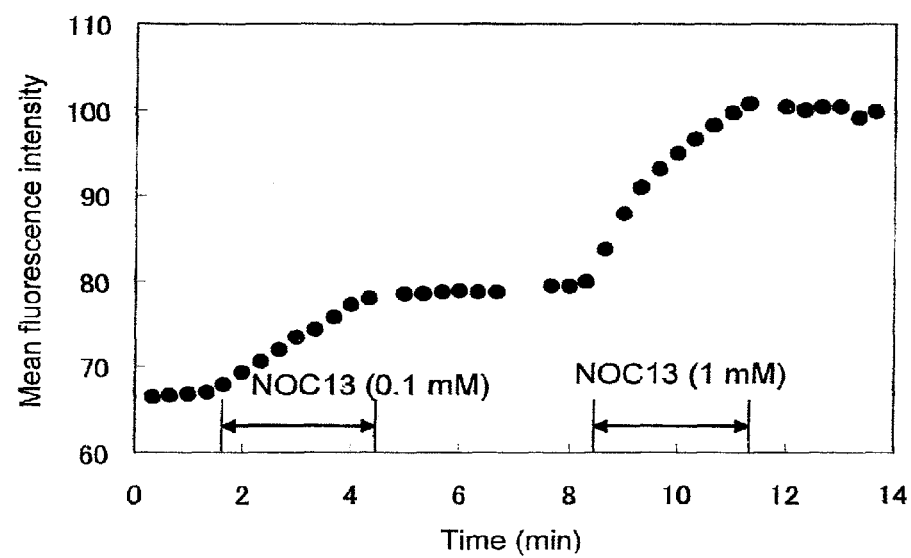
FIG. 5 shows change of fluorescence intensity of the compound 2 caused by addition of a nitrogen monoxide donor.

A perfusate was flown from the right kidney aorta of anesthetized rat, and then the right kidney was quickly extracted and placed on a stage of a stereoscopic fluorescence microscope, which was capable of observation in the near-infrared region (excitation filter: 730±23 nm, fluorescence filter: 770 nm long-pass). When a solution of the compound 2 was introduced into the right kidney instead of the perfusate, weak fluorescence was measurable from the outside of the kidney, and thus it was confirmed that the compound 2 was loaded on the inside of the kidney. A near-infrared fluorescence image of the inside of the kidney taken from the outside of the kidney is shown in FIG. 4. A round structure considered to originate in capillaries around the glomeruli existing in the inside of the kidney was observed. Then, fluorescence images were obtained every 20 seconds with alternately flowing the perfusate and a solution of the nitrogen monoxide donor (NOC13). Average of fluorescence intensity of the whole field of each image was calculated, and the temporal change thereof was observed. As a result, it was confirmed that the fluorescence intensity was increased only while the nitrogen monoxide donor was given (FIG. 5).

From the above results, it was verified that the compound 2 had an ability to detect nitrogen monoxide even in an environment of living tissue, and inside of living tissue was observable from the outside by utilizing fluorescence of the near-infrared region.

Industrial Applicability

The compound of the present invention has a property of very efficiently reacting with nitrogen monoxide and a metal ion (zinc ion and the like) to give a fluorescence substance, and the fluorescence substance emits extremely intense fluorescence by excitation with light of the near-infrared region. Therefore, by using the compound as a fluorescent probe, it becomes possible to measure nitrogen monoxide or metal ions in a deep tissue of a living body.

What is claimed is:

1. A compound represented by the following general formula (IA):

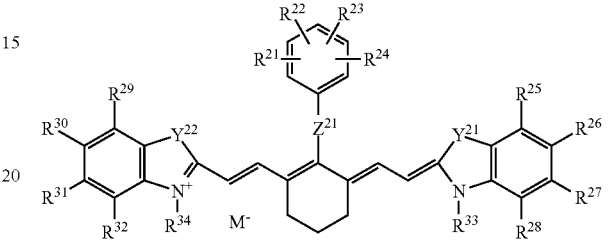

(IA)

wherein $R^{21}$ and $R^{22}$ represent amino groups substituting at adjacent positions on the benzene ring, and one of the amino groups may have one alkyl group which may have a substituent; $R^{23}$ and $R^{24}$ independently represent a hydrogen atom, a $C_{1-6}$ alkyl group which may have a substituent, or a $C_{1-6}$ alkoxy group which may have a substituent; $R^{25}$, $R^{26}$, $R^{27}$, $R^{28}$, $R^{29}$, $R^{30}$, $R^{31}$, and $R^{32}$ independently represent a hydrogen atom, a sulfo group, a phospho group, a halogen atom, or a $C_{1-6}$ alkyl group which may have a substituent; $R^{33}$ and $R^{34}$ independently represent a $C_{1-18}$ alkyl group which may have a substituent; $Z^{21}$ represents an oxygen atom, a sulfur atom, or —N($R^{35}$)— wherein $R^{35}$ represents a hydrogen atom, or a $C_{1-6}$ alkyl group which may have a substituent; $Y^{21}$ and $Y^{22}$ independently represent —C(=O)—, —C(=S)—, or —C($R^{36}$)($R^{37}$)— wherein $R^{36}$ and $R^{37}$ independently represent a $C_{1-6}$ alkyl group which may have a substituent; and $M^-$ represents a counter ion in a number required for neutralizing the charge.

2. The compound according to claim 1, wherein $R^{23}$, $R^{24}$, $R^{25}$, $R^{26}$, $R^{27}$, $R^{28}$, $R^{29}$, $R^{30}$, $R^{31}$, and $R^{32}$ are hydrogen atoms, $R^{33}$ and $R^{34}$ are $C_{1-6}$ alkyl groups substituted with a sulfo group, $Z^{21}$ is an oxygen atom, and $Y^{21}$ and $Y^{22}$ are —C(CH$_3$)$_2$—.

3. A reagent for measuring nitrogen monoxide, which contains the compound represented by the general formula (IA) according to claim 1.

4. A method for measuring nitrogen monoxide, which comprises (a) reacting the compound represented by the general formula (IA) with nitrogen monoxide;

(IA)

wherein $R^{21}$ and $R^{22}$ represent amino groups substituting at adjacent positions on the benzene ring, and one of the amino groups may have one alkyl group which may have a substituent; $R^{23}$ and $R^{24}$ independently represent a hydrogen atom, a $C_{1-6}$ alkyl group which may have a substituent, or a $C_{1-6}$ alkoxy group which may have a substituent; $R^{25}$, $R^{26}$, $R^{27}$, $R^{28}$, $R^{29}$, $R^{30}$, $R^{31}$, and $R^{32}$ independently represent a hydrogen atom, a sulfo group, a phospho group, a halogen atom, or a $C_{1-6}$ alkyl group which may have a substituent; $R^{33}$ and $R^{34}$ independently represent a $C_{1-18}$ alkyl group which may have a substituent; $Z^{21}$ represents an oxygen atom, a sulfur atom, or —N($R^{35}$)—, wherein $R^{35}$ represents a hydrogen atom, or a $C_{1-6}$ alkyl group which may have a substituent; $Y^{21}$ and $Y^{22}$ independently represent —C(=O)—, —C(=S)—, or —C($R^{36}$)($R^{37}$)—, wherein $R^{36}$ and $R^{37}$ independently represent a $C_{1-6}$ alkyl group which may have a substituent; and M⁻ represents a counter ion in a number required for neutralizing the charge; and (b) detecting the compound of the general formula (IB)

(IB)

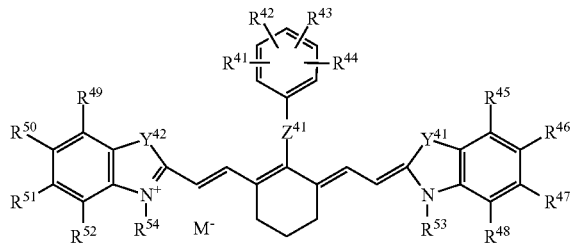

wherein $R^{41}$ and $R^{42}$ combine together to represent a group represented by —N=N—NR$^{58}$— which forms a ring at the adjacent positions on the benzene ring, wherein $R^{58}$ represents a hydrogen atom, or a $C_{1-6}$ alkyl group which may have a substituent, or $R^{41}$ and $R^{42}$ represent a combination of an amino group which may have a $C_{1-6}$ alkyl group which may have a substituent, or a protective group for an amino group; and a nitro group substituting at adjacent positions on the benzene ring; $R^{43}$ and $R^{44}$ independently represent a hydrogen atom, a $C_{1-6}$ alkyl group which may have a substituent, or a $C_{1-6}$ alkoxy group which may have a substituent; $R^{45}$, $R^{46}$, $R^{47}$, $R^{48}$, $R^{49}$, $R^{50}$, $R^{51}$, and $R^{52}$ independently represent a hydrogen atom, a sulfo group, a phospho group, a halogen atom, or a $C_{1-6}$ alkyl group which may have a substituent; $R^{53}$ and $R^{54}$ independently represent a $C_{1-18}$ alkyl group which may have a substituent; $Z^{41}$ represents an oxygen atom, a sulfur atom, or —N($R^{55}$)—, wherein $R^{55}$ represents a hydrogen atom, or a $C_{1-6}$ alkyl group which may have a substituent; $Y^{41}$ and $Y^{42}$ independently represent —C(=O)—, —C(=S)—, or —C($R^{56}$)($R^{57}$)—, wherein $R^{56}$ and $R^{57}$ independently represent a $C_{1-6}$ alkyl group which may have a substituent; and M⁻ represents a counter ion in a number required for neutralizing the charge; wherein $R^{41}$ and $R^{42}$ combine together to represent a group represented by —N=N—NR$^{58}$— which forms a ring at the adjacent positions on the benzene ring wherein $R^{58}$ represents a hydrogen atom, or a $C_{1-6}$ alkyl group which may have a substituent produced in (a).

\* \* \* \* \*